United States Patent
Maroofian et al.

(10) Patent No.: US 10,945,470 B1
(45) Date of Patent: Mar. 16, 2021

(54) FACE SHIELD

(71) Applicant: Pinnpack Packaging, LLC, Oxnard, CA (US)

(72) Inventors: Ira Maroofian, Oxnard, CA (US); Chris Mair, Oxnard, CA (US)

(73) Assignee: PINNPACK PACKAGING, LLC, Oxnard, CA (US)

( * ) Notice: Subject to any disclaimer, the term of this patent is extended or adjusted under 35 U.S.C. 154(b) by 0 days.

(21) Appl. No.: 16/914,465

(22) Filed: Jun. 28, 2020

Related U.S. Application Data

(60) Provisional application No. 63/021,724, filed on May 8, 2020.

(51) Int. Cl.
  *A41D 13/11* (2006.01)

(52) U.S. Cl.
  CPC ...... *A41D 13/1184* (2013.01); *A41D 13/1107* (2013.01); *A41D 13/1161* (2013.01)

(58) Field of Classification Search
  CPC ............ A41D 13/1184; A41D 13/1161; A41D 13/1107
  See application file for complete search history.

(56) References Cited

U.S. PATENT DOCUMENTS

| | | | | |
|---|---|---|---|---|
| 460,301 A * | 9/1891 | Cumnock | ............... | A61F 9/02 2/9 |
| 2,426,266 A * | 8/1947 | Haas | ............... | G02C 7/10 2/450 |
| 3,214,767 A * | 11/1965 | Weber | ............... | A61F 9/06 2/9 |
| 3,613,115 A * | 10/1971 | Hill | ............... | A61F 9/025 2/10 |
| 3,686,690 A * | 8/1972 | Webb | ............... | A42B 3/225 2/9 |
| 4,825,878 A * | 5/1989 | Kuntz | ............... | A41D 13/11 128/207.11 |
| 4,853,974 A * | 8/1989 | Olim | ............... | A41D 13/1184 2/9 |
| 4,867,178 A * | 9/1989 | Smith | ............... | A41D 13/1184 128/858 |
| 4,884,296 A * | 12/1989 | Nix, Jr. | ............... | A61F 9/02 2/11 |
| 4,944,312 A * | 7/1990 | Smith | ............... | A41D 13/1161 128/207.11 |
| 4,945,573 A * | 8/1990 | Landis | ............... | A61F 9/02 128/863 |
| 4,945,574 A * | 8/1990 | Dagher | ............... | A61F 9/02 128/201.12 |

(Continued)

OTHER PUBLICATIONS

Inc. Magazine, these two companies are making face shields for everyone,Apr. 6, 2020, Inc. Magazine, 5000, All pages (Year: 2020).*

*Primary Examiner* — Khaled Annis
(74) *Attorney, Agent, or Firm* — Michael R Shevlin

(57) ABSTRACT

A disposable face shield designed to protect the eyes and face of wearers from various diseases, such as COVID-19. The face shield assembly includes a transparent shield panel coupled with a front strap and back strap. The front strap contacts the forehead and spaces the transparent shield panel away from the face. The back strap extends around the head and holds the transparent shield panel on the head. Each of the straps are adjustable for different type head sizes.

20 Claims, 8 Drawing Sheets

(56) References Cited

U.S. PATENT DOCUMENTS

| | | | | |
|---|---|---|---|---|
| 5,113,528 | A * | 5/1992 | Burke, Jr. | A61F 9/02 128/857 |
| 5,138,714 | A * | 8/1992 | Smith | A61F 9/02 128/206.23 |
| 5,337,419 | A * | 8/1994 | Russell | A61F 9/02 128/857 |
| 5,440,760 | A * | 8/1995 | Highsmith | A41D 13/11 128/857 |
| 5,765,223 | A * | 6/1998 | McCausland | A61F 9/02 2/426 |
| 5,970,514 | A * | 10/1999 | Wang-Lee | A61F 9/045 2/10 |
| 5,983,390 | A * | 11/1999 | Desy | A41D 13/1161 128/858 |
| 8,756,715 | B1 * | 6/2014 | Moffitt, Jr. | A42B 3/24 2/171.3 |
| 9,427,288 | B1 * | 8/2016 | Chenger | A61B 90/05 |
| 2005/0251890 | A1 * | 11/2005 | Landis | A61F 9/022 2/9 |
| 2009/0241855 | A1 * | 10/2009 | Stocki | A01K 13/006 119/815 |
| 2010/0031962 | A1 * | 2/2010 | Chiu | A62B 23/025 128/206.19 |
| 2011/0265236 | A1 * | 11/2011 | Stoll | A41D 13/1184 2/9 |
| 2012/0047614 | A1 * | 3/2012 | Choi | A41D 13/1184 2/9 |
| 2015/0128323 | A1 * | 5/2015 | Howard | A41D 13/1184 2/9 |
| 2015/0237931 | A1 * | 8/2015 | Miller | A41D 13/1184 2/9 |
| 2016/0143378 | A1 * | 5/2016 | Howard | A41D 13/1184 2/9 |

\* cited by examiner

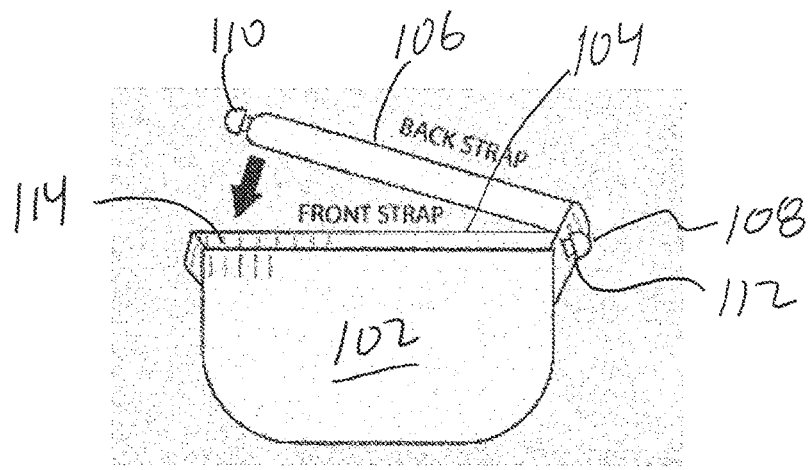
FIG. 3A
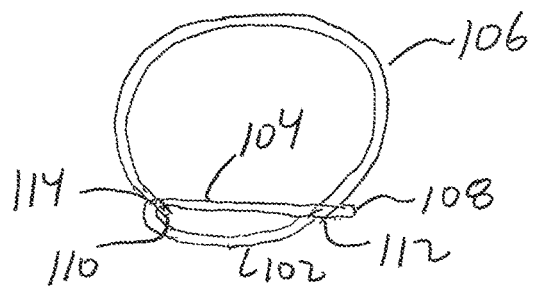
FIG. 3B
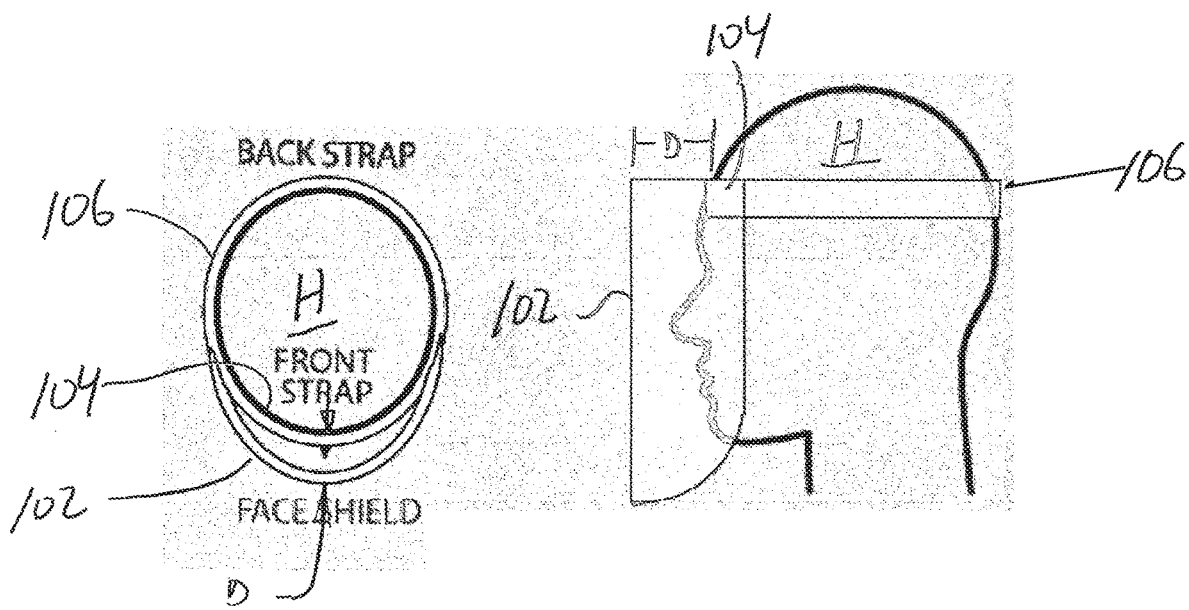
FIG. 4A
FIG. 4B

STEP 1

TAKE THE FRONT STRAP, WHICH WILL GO ACROSS THE FOREHEAD, AND SLIDE IT INTO ONE OF THE NOTCHES ON THE BACK STRAP

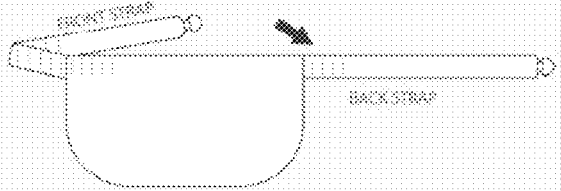

STEP 2

TAKE THE BACK STRAP, WHICH WILL GO BEHIND YOUR HEAD, AND SLIDE IT INTO ONE OF THE NOTCHES ON THE FRONT STRAP. FIND THE NOTCH THAT FITS YOUR HEAD SIZE

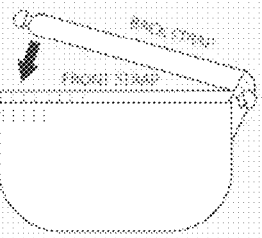

STEP 3

SLIDE THE FINISHED MASK OVER YOUR HEAD AND FACE. THE FRONT STRAP WILL GO ACROSS THE FOREHEAD AND THE BACK STRAP WILL GO BEHIND YOUR HEAD

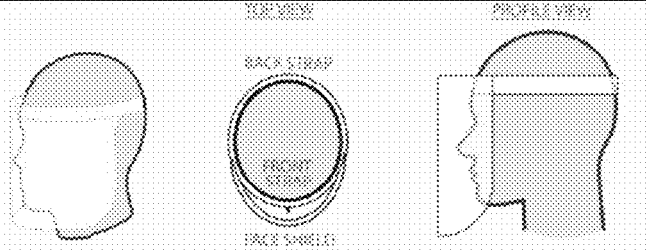

FIG. 5

Inside View – Into the Mask

Outside View Looking at Mask

FACE SHIELD

CROSS REFERENCE TO RELATED APPLICATIONS

This application claims priority from U.S. Provisional Patent Application No. 63/021,724, filed on May 8, 2020, the contents of which is incorporated herein by reference.

FIELD

The present invention relates to a face shield to protect the face and eyes of the wearer from various viruses, and more particularly, the invention is directed to a face shield from various viruses that includes a feature to position the face shield away from the face.

BACKGROUND

Medical and dental care professionals are exposed to infectious pathogens on a daily basis. With the spread of various viruses, such as COVID-19, and diseases, many that are deadly and presently incurable, the protection of these professionals has become more vital than ever. Many of the viruses and diseases come from nasal and oral emissions, blood, and other bodily fluids. Because the eyes, nose and mouth include regions of thin and penetrable membranes, the face is an area requiring appropriate protection from flying contaminants and particulates.

Several requirements must be met by a facial protection device of this type. It must be light weight and easily worn and removed. It must adequately shield the vital areas of the face yet not obstruct vision. It must provide ample ventilation as not to hamper breathing and to further avoid fogging and accumulation of moisture. In addition, it should be disposable for adequate and safe disposition of contaminants.

There is thus a need for a face shield which is capable of being comfortably worn which will protect the desired areas of the face and eyes

SUMMARY OF THE INVENTION

Embodiments described herein may meet one or more of the needs identified above and may overcome one or more of the shortcomings of current containers. Various implementations of systems, methods, and devices within the scope of the appended claims each have several aspects, no single one of which is solely responsible for the desirable attributes described herein. Without limiting the scope of the appended claims, some prominent features are described herein.

The present invention is a face shield that is design to protect the eyes and face of wearers from accidental exposure to infectious, hazardous, and undesirable substances. The face shield includes a transparent shield panel coupled with a front strap and a back strap. The front strap contacts the forehead to position the transparent shield panel away from the face. The back strap extends around the head and holds the transparent shield panel on the head. Each of the straps are adjustable for different type head sizes.

To assemble the disposable face shield, the front strap is bowed behind the shield panel and a front strap attachment feature is inserted into a front strap attachment slot. The back strap is then bowed in the opposite direction and a back strap attachment feature is inserted into a back strap attachment slot. There are multiple front strap attachment slots to provide various offsets of the transparent shield panel from the face and various back strap attachment slots to accommodate various size heads.

In use, the front strap is bowed and the front strap attachment feature is inserted into the desired front strap attachment slot. The transparent shield panel is then positioned on the face and pushed inward slightly with the front strap flexing in a spring-like manner as it makes contact with the forehead. Once the desired offset distance of the shield is achieved, the back strap is then bowed around the back of the head and the back strap attachment feature is inserted into the appropriate back strap slot that will hold the face shield on the head.

Although intended primarily for use by such health care professionals, the protective face shield of the present invention may be used to protect the face and eyes from metallic particles, rock chips, dust, paint splatters, and the like, generated in the course of carrying out a myriad of household and industrial tasks.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE DRAWINGS

The present embodiments may be understood from the following detailed description when read in conjunction with the accompanying figures. It is emphasized that the various features of the figures are not necessarily to scale. On the contrary, the dimensions of the various features may be arbitrarily expanded or reduced for clarity.

FIGS. 3A-3B are front and top views showing the back strap bowed into the use position.

FIGS. 4A-4B are top and side views showing the face shield attached to a head with the front strap contacting the forehead and the back strap holding the face shield on the head.

FIG. 5 shows a method of using the face shield shown in FIG. 1.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
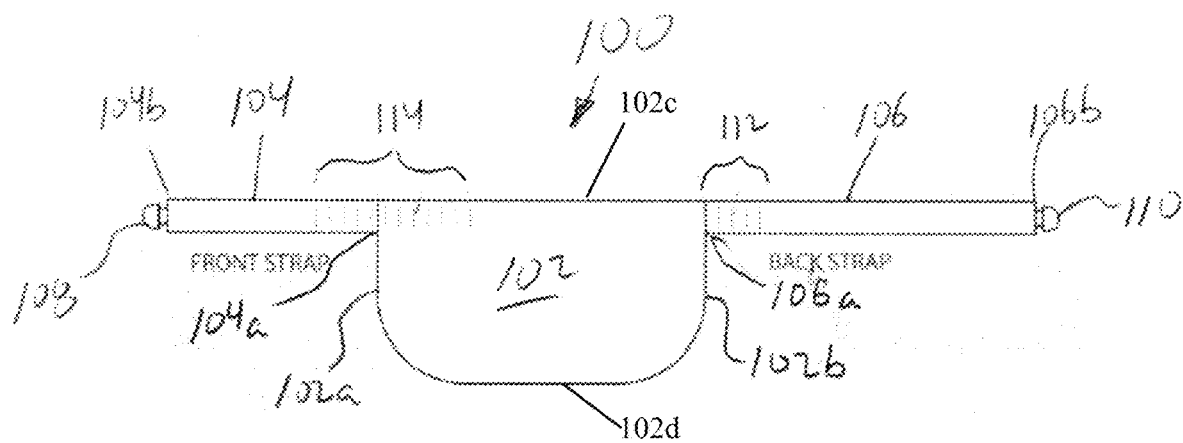
FIG. 1 is a front view showing one embodiment of a face shield in a flat position.

FIG. 1 is a front view showing one embodiment of a one-piece face shield 100 having a transparent shield panel 102, a front strap 104, and a back strap 106. The face shield 100 is preferably made of a flexible plastic material and the transparent shield panel 102 is sized to cover the desired portion of a person's head. In the embodiment shown, the transparent shield panel 102 is sized to cover the width of the face and extends from the forehead to chin. In other embodiments, the transparent shield panel 102 may extend higher than the forehead or lower than the chin. In other embodiments, the transparent shield panel 102 may shorter than the chin and only cover a portion of the face, such as the nose and mouth. The transparent shield panel 102 includes a first side edge 102a, a second side edge 102b, a top edge 102c and a bottom edge 102d. In the embodiment shown, the edges are shaped essentially straight with parallel side edges and parallel top and bottom edges. In other embodiments, the shape of the transparent shield panel 102 and the edges may have non-straight shapes, such as curved or wavy, and non-parallel sides.

The front strap 104 includes a first end 104a and a second end 104b. The front strap 104 integrally extends from the first side edge 102a of the transparent shield panel 102 at the first end 104a, and the second end 104b having a front strap attachment feature 108. The back strap 106 includes a first end 106a and a second end 106b. The back strap 106 integrally extends from the second side edge 102b of the transparent shield panel 102 at the first end 106a, and a second end 106b having a back strap attachment feature 110. The face shield 100 further includes multiple transparent shield panel attachment features 112, 114 configured to couple with the front strap attachment feature 108 and the back strap attachment feature 110.

In the embodiment shown, the front strap 104 and back strap 106 are different lengths. The front strap 104 is designed to be bowed toward the interior or face side of the transparent shield panel 102 with the front strap attachment feature 108 coupling with the transparent shield panel attachment feature 112 proximate the second side edge 102b of the transparent shield panel 102, creating a space between them forming a distance D between the transparent shield panel 102 and the front strap 104. The front strap 104 may be lengthened or shortened to vary the distance D, so that the transparent shield panel 102 does not contact any face features, such as the nose or glasses. The back strap 106 to designed to go around the back of the head with the back strap attachment feature 110 coupling with the transparent shield panel attachment feature 114 proximate the first side edge 102a of the transparent shield panel 102. The back strap 106 may be lengthened or shortened to vary the size to fit on different size heads. In use, the front strap 104 contacts the forehead and the space between the transparent shield panel 102 and the front strap 104 positions the transparent shield panel 102 a distance D away from the face, and the back strap 106 holds the face shield 100 on the head (see FIG. 4).

In the embodiment shown in FIG. 1, the face shield 100 is a one-piece design with a transparent shield panel 102, an integral front strap 104, and integral back strap 106. The front strap 104 and back strap 106 extend outwardly from opposite first and second side edges 102a, 102b of the transparent shield panel 102. In other embodiments, the front strap 104 and back strap 106 may extend outwardly from any location along the side edges 102a, 102b. In other embodiments, the face shield 100 may include separate components, with the first ends 104a and 106a of front strap 104 and back strap 106 attached to the side edges 102a, 102b using known attachment methods, such as bonding, welding, gluing, riveting, stapling, fastening, etc.

In the embodiment shown in FIG. 1, the transparent shield panel attachment features 112, 114 are attachment slots and the front strap attachment feature 108 and back strap attachment feature 110 are hooks or tabs (see FIGS. 1 and 6) configured to slide into the attachment slots and lock the second ends 104b, 106b in place. In other embodiments, the front strap attachment feature 108, back strap attachment feature 110, and the transparent shield panel attachment features 112, 114 may use other attachment means, such as adhesive or Velcro.

In some embodiments the shield panel 102, the front strap 104 and the back strap 106 may be made using a lightweight clear flexible sheet material that is optically clear. It is also desirable that the flexible material is sufficiently rigid to be self-supporting when bowed in a cylindrical shape to cover the face without collapsing. The face shield 100 may be made of any clear flexible material, such as PVC, PET, PETG, OPS, Polycarbonate and APET. The thickness of the material will depend on the particular material used to ensure sufficient flexibility without sacrificing the need of the material to be self supporting. The material selected is generally inexpensive such that the shield can be manufactured or fabricated at a low cost and be disposed of after each use. The one-piece face shield 100 may be made using known means, such as: molded, formed or die-cut. The one-piece face shield 100 may be made or fabricated as a flat sheet flat and cut and may include curvature.

In other embodiments the shield panel 102 is made of a first material and the front strap 104 and/or the back strap 106 is made of a second material. The first material may be made using a lightweight clear flexible material that is optically clear and the second material may be a flexible material that is non-optically clear. It is also desirable that the flexible material is sufficiently rigid to be self-supporting when bowed in a cylindrical shape to cover the face without collapsing.

Figure 2A:
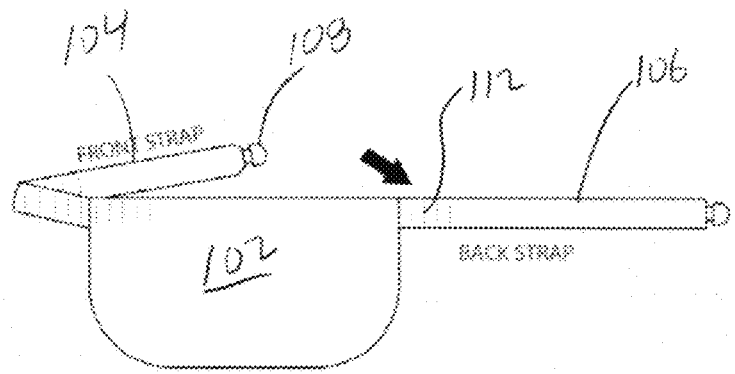
FIGS. 2A-2*b* are front and top views showing the front strap bowed into the use position.
Figure 2B:
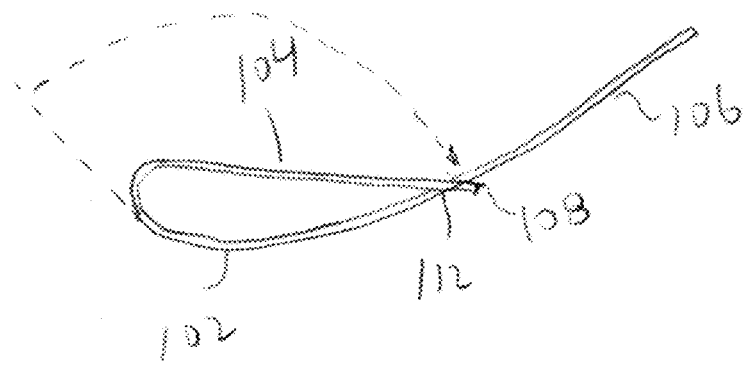

FIGS. 2A-2B are front and top views showing features of the front strap 104. The front strap 104 to designed to contact the forehead and position the transparent shield panel 102 a distance D away from the face (see FIG. 4). The front strap 104 is made of materials that provide flexibility and some rigidity so that front strap 104 may conform to the contours of the forehead. The front strap 104 includes an adjustment feature to vary the distance D so that the transparent shield panel 102 does not contact any face features, such as the nose.

To start assembly of the face shield 100, the front strap 104 is bowed behind the transparent shield panel 102 and the front strap attachment feature 108 is inserted into one of the transparent shield panel attachment slots 112. There are multiple transparent shield panel attachment slots to provide various offsets of the transparent shield panel from the face.

FIGS. 3A-3B are front and top views showing features of the back strap 106. The back strap 106 to designed to go around the back of the head to hold the face shield 100 on the head (see FIG. 4). The back strap 106 is made of materials that provide flexibility to form to the contours around head. The back strap 106 includes adjustment features 110 that couple with the transparent shield panel attachment slots 114 to vary sizing of the face shield 100 to fit different size heads.

The back strap 106 is usually assembled after the front strap 104. The back strap 106 is bowed behind the transparent shield panel 102 in an opposite direction than the front strap 104. The back strap attachment feature 110 is inserted into one of the transparent shield panel attachment slots 114. There are multiple transparent shield panel attachment slots 114 to provide various size options to accommodate various size heads.

FIGS. 4A-4B are top and side views showing the face shield 100 attached to a head H. In use, the front strap 104 is bowed and the front strap attachment feature 108 is inserted into the desired transparent shield panel attachment slot 112. The transparent shield panel 102 is then positioned on the face and pushed inward slightly with the front strap 104 flexing in a spring-like manner as it makes contact and conforms with the forehead. The back strap 106 is then bowed around the back of the head and the back strap attachment feature 110 is inserted into the appropriate transparent shield panel attachment slot 114 that will hold the face shield 100 on the head H.

FIG. 5 shows a method of assembling the face shield 100 and attaching the face shield 100 to a head H. In Step 1, take the front strap 104 which will go across the forehead and bow it behind the transparent shield panel 102 and slide the front strap attachment feature 108 into one of the transparent shield panel attachment slots 112. In Step 2, take the back strap 106, which will go behind the head H, and find the transparent shield panel attachment slot 114 that fits the head size, and slide the back strap attachment feature 110 into the selected attachment slot 114. In Step 3, slide the finished face mask 100 over the head H and face. The front strap 104 will go across the forehead, flexing in a spring-like manner as it makes contact and conforms with the forehead, and the back strap 106 will go behind the head H to hold the face shield 100 on the head H.

Figure 6:
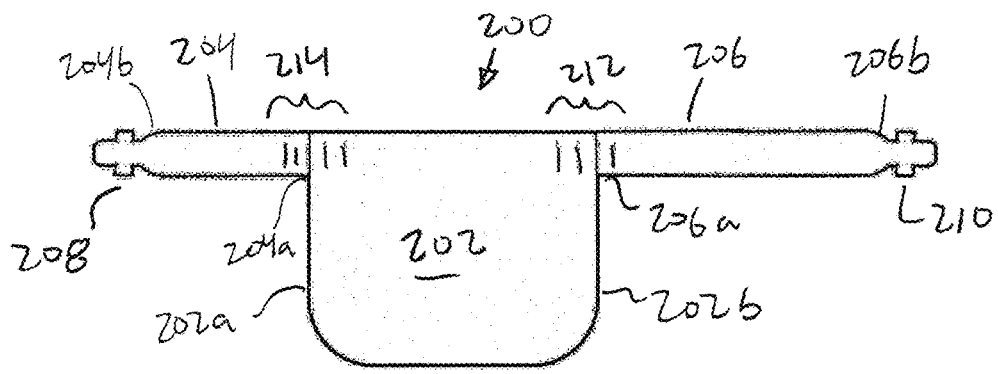
FIG. 6 is a front view showing another embodiment of a face shield in a flat position.

FIG. 6 is a front view showing another embodiment of a face shield 200 that is similar to face shield 100. Face shield 200 includes a transparent shield panel 202, a front strap 204, and a back strap 206. The transparent shield panel 202 is preferably made of a flexible plastic material and is sized to cover to width of the face and extend from the forehead to chin. The front strap 204 includes a first end 204a coupled to a first side edge 202a of the transparent shield panel 202 and an opposite second end 204b having a front strap attachment feature 208. The back strap 206 includes a first end 206a coupled to a second side edge 202b of the transparent shield panel 202 and a second end 206b having a back strap attachment feature 210. The face shield 200 further includes multiple transparent shield panel attachment slots or slits 212 configured to couple with the front strap attachment feature 208 and transparent shield panel attachment slots or slits 214 configured to couple with the back strap attachment feature 210.

Figure 10:
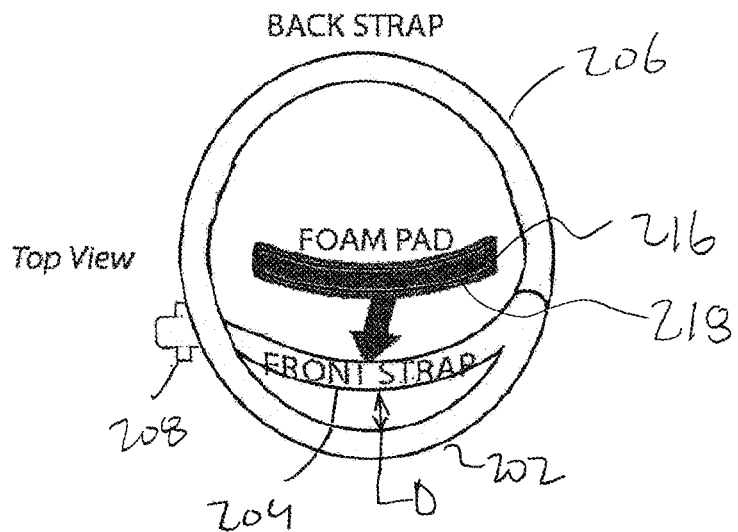
FIG. 10 is a top showing the assembled face shield.

The face shield 200 is designed to use the front strap 204 to contact the forehead and position the transparent shield panel 202 away from the face a distance D (see FIG. 10). The front strap 204 is made of materials that provide flexibility and some rigidity so that front strap 204 may conform to the contours of the forehead. The front strap 204 includes adjustment features to vary the distance D so that the transparent shield panel 202 does not contact any face features, such as the nose.

In the embodiment shown in FIG. 6, the face shield 200 is a one-piece design with an integral front strap 204 and integral back strap 206, the front strap 204 and back strap 206 integrally extending outwardly from opposite first and second side edges 202a, 202b proximate the top of the transparent shield panel 202. In other embodiments, the front strap 204 and back strap 206 may extend outwardly from any location along the side edges 202a, 202b. In other embodiments, the face shield 200 may include separate components, with the first ends 204a and 206a of front strap 204 and back strap 206 attached to the side edges 202a, 202b using known attachment methods, such as bonding, welding, gluing, riveting, stapling, fastening, etc.

In the embodiment shown in FIG. 6, the and the front strap attachment feature 208 and back strap attachment feature 210 are lock notches or lock tabs configured to slide into transparent shield panel attachment slots 212, 214 and lock the ends 204b, 206b in place. In other embodiments, the second ends of the front strap and back strap may use other attachment means to the shield panel, such as adhesive or Velcro.

The shield panel 202 may be made using a lightweight clear flexible sheet material that is optically clear. It is also desirable that the flexible material is sufficiently rigid to be self-supporting when bowed in a cylindrical shape to cover the face without collapsing. The face shield 200 may be made of any clear flexible material that includes anti-fog properties, is durable and lightweight, and is disposable, recyclable, and/or reusable. The material may be plastic, such as PVC, PET, PETG, OPS, Polycarbonate and APET. The thickness of the material will depend on the particular material used to ensure sufficient flexibility without sacrificing the need of the material to be self supporting. The material selected is generally inexpensive such that the shield can be manufactured or fabricated at a low cost.

Figures 7A, 7B:
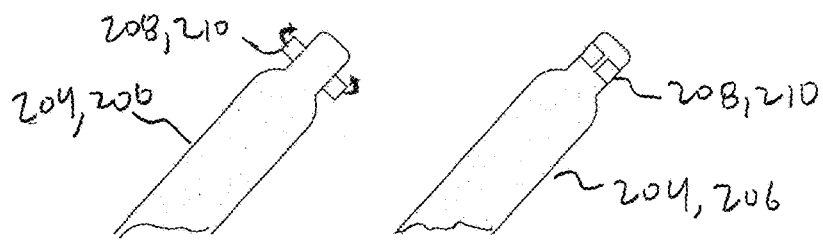
FIGS. 7A-7B show attachment features in the open position and insertion position.

FIG. 7A shows front and rear strap attachment lock notches or lock tabs 208, 210 of front and back straps 204, 206 in the open position and FIG. 7B shows the lock notches or lock tabs 208, 210 in the insertion position. In the open position, the front and rear strap attachment lock notches or lock tabs 208, 210 are too wide the slide into transparent shield panel attachment slots 212, 204. Prior to sliding into transparent shield panel attachment slots 212, 214, the front and rear strap attachment lock notches or lock tabs 208, 210 are prepared by bending or folding them inward toward each other, shown in FIG. 7B. The allows the front and rear strap attachment lock notches or lock tabs 208, 210 to slide easily into transparent shield panel attachment slots 212, 214. Once through the transparent shield panel attachment slots 212, 214 the front and rear strap attachment lock notches or lock tabs 208, 210 are unfolded or bent open to prevent pullout, thereby locking the attachment lock notches or lock tabs 208, 210 in the attachment slots 212, 214, shown in FIGS. 8B, 9B. If the size needs to be changed, the attachment lock notches or lock tabs 208, 210 may be bent or folded again and then withdrawn from the attachment slots 212, 214.

Figures 8A, 8B:
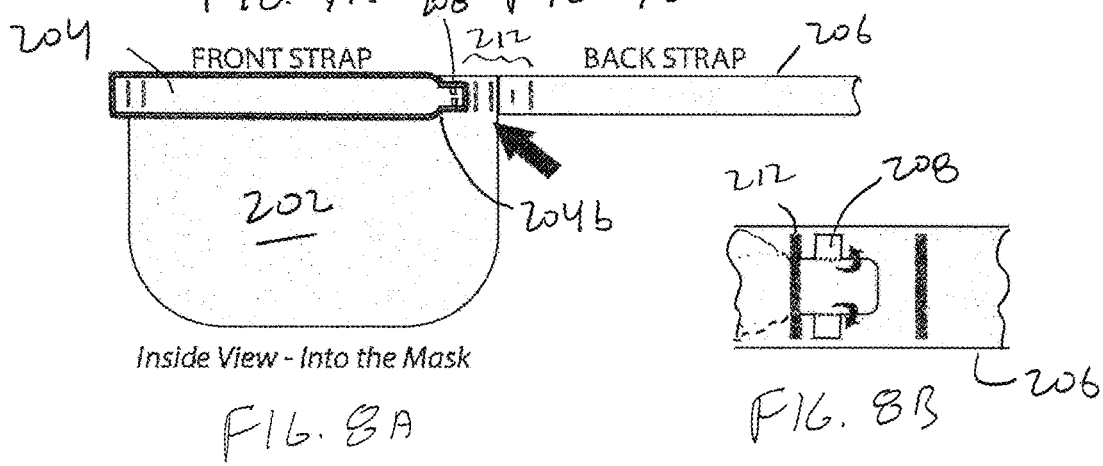
FIG. 8A is an inside view looking into the mask showing attachment of the front strap and FIG. 8B is an enlarged view showing engagement of the attachment feature with attachment slot.

FIG. 8A is an inside view looking into the mask showing attachment of the front strap 204 and FIG. 8B is an enlarged view showing engagement of the attachment feature 208 with transparent shield panel attachment slot 212. The front strap 204 to designed to contact the forehead and position the transparent shield panel 202 a distance D away from the face. The front strap 204 is made of materials that provide flexibility and some rigidity so that front strap 204 may conform to the contours of the forehead. The front strap 204 includes an adjustment feature to vary the distance D so that the transparent shield panel 202 does not contact any face features, such as the nose.

To start assembly of face shield 200, front strap 204 is bowed on the face side of transparent shield panel 202 and front strap attachment lock notch or lock tab 208 is inserted into one of the transparent shield panel attachment slots 212. Once the attachment lock notch or lock tab 208 is inserted through the selected transparent shield panel attachment slot 212, the attachment lock notch or lock tab 208 is unfolded to lock it in the attachment slot 212, shown in FIG. 8B. There are multiple transparent shield panel attachment slots 212 to provide various offsets or distance D of the transparent shield panel from the face. If the size needs to be changed, the attachment lock notch or lock tab 208 may be bent or folded again and then withdrawn from the transparent shield panel attachment slot 212.

Figures 9A, 9B:
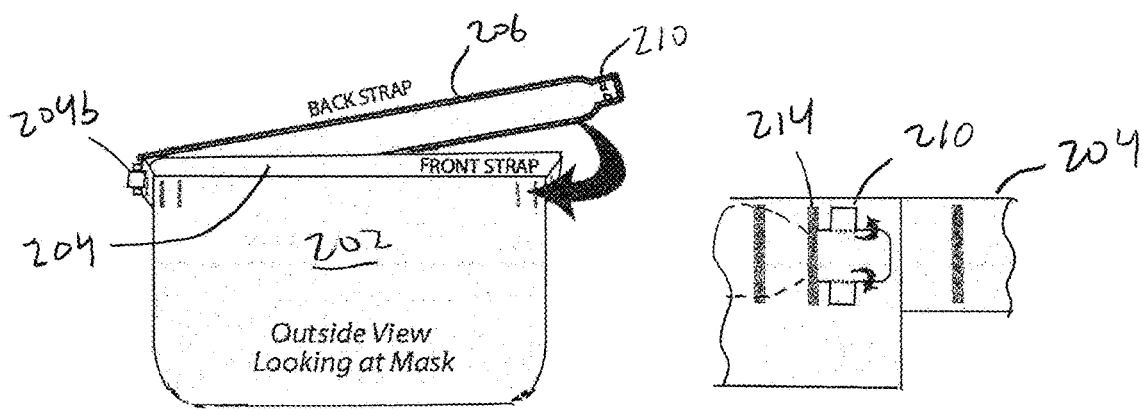
FIG. 9A is an outside view looking at face mask showing attachment of the back strap.
FIG. 9B is an enlarged view showing engagement of the attachment feature with attachment slot.

FIG. 9A is an outside view looking at face mask 200 showing attachment of the back strap 206, and FIG. 9B is an enlarged view showing engagement of the attachment lock notch or lock tab 210 with transparent shield panel attachment slot 214. The back strap 206 to designed to go around the back of the head H to hold the face shield 200 on the head (see FIGS. 11A, 11B). The back strap 206 is made of materials that provide flexibility to form to the contours around head. The back strap 206 includes adjustment features 210 that couple with the transparent shield panel attachment slot 214 to vary sizing of the face shield 200 to fit different size heads.

The back strap 206 is usually assembled after the front strap 204. The back strap 206 is bowed behind the transparent shield panel 202 in an opposite direction than the front strap 204. The back strap attachment lock notch or lock tab 210 is then inserted into one of the transparent shield panel attachment slots 214 in the bent or folded position, shown in FIG. 7B. There are multiple transparent shield panel attachment slots 214 to provide various size options to accommodate various size heads. Once the attachment feature 210 is inserted through the selected transparent shield panel attachment slot 214, attachment feature 210 is unfolded to lock it in the transparent shield panel attachment slot 214, shown in FIG. 9B.

FIG. 10 is a top showing the assembled face shield 200. The front strap 204 is bowed on the rear or face side of transparent shield panel 202. The distance D may be varied by sliding the front strap attachment feature 208 into the various transparent shield panel attachment slots 112. When the desired distance is achieved, the front strap attachment feature 208 is unfolded in the desired transparent shield panel attachment slot 212, locking it in place. The back strap 206 is bowed behind the transparent shield panel 202 in an opposite direction than the front strap 204 and the back strap attachment feature 210 is then inserted into the desired transparent shield panel attachment slot 214 and locked in place. There are multiple transparent shield panel attachment slots 214 to provide various size options to accommodate various size heads. If the size needs to be changed, the attachment feature 210 may be bent or folded again and then withdrawn from the transparent shield panel attachment slot 214.

An optional pad 216 may be used inside the front strap 204 to contact the head H. The pad 216 includes an attachment material 218 that is used to attach the pad 216 with the front strap 204. The pad 216 may be made of different material depending on the application. The strap may be made of a soft material for comfort, made of a frictional material to prevent slippage of the face mask 200 on the head, or made of an absorbent material to soak up sweat to keep it out of the eyes, similar to a headband. In the embodiment shown, the pad 216 is a foam material. The attachment material 218 may be an adhesive material, such as an adhesive strip, or may be a Velcro material so the pad 216 removable or replaceable.

Figure 11A:
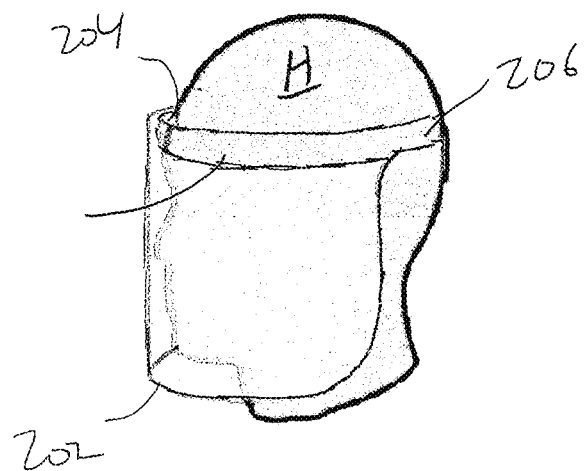
FIGS. 11A-11B are top and side views showing the face shield attached to a head with the front strap contacting the forehead and the back strap holding the face shield on the head.
Figure 11B:
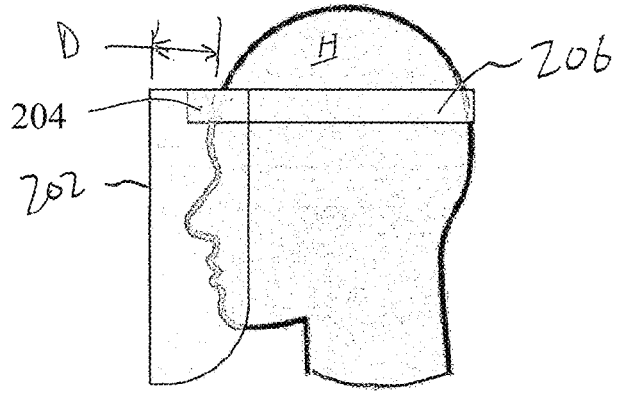

FIGS. 11A-11B are perspective and side views showing the face shield 200 attached to a head H. In use, the front strap 204 is bowed and the front strap attachment feature 208 is inserted into the desired transparent shield panel attachment slot 212. The transparent shield panel 202 is then positioned on the face and pushed inward slightly with the front strap 204 flexing in a spring-like manner as it makes contact and conforms with the forehead. The back strap 206 is then bowed around the back of the head and the back strap attachment feature 210 is inserted into the appropriate transparent shield panel attachment slot 214 that will hold the face shield 200 on the head H.

Figure 12:
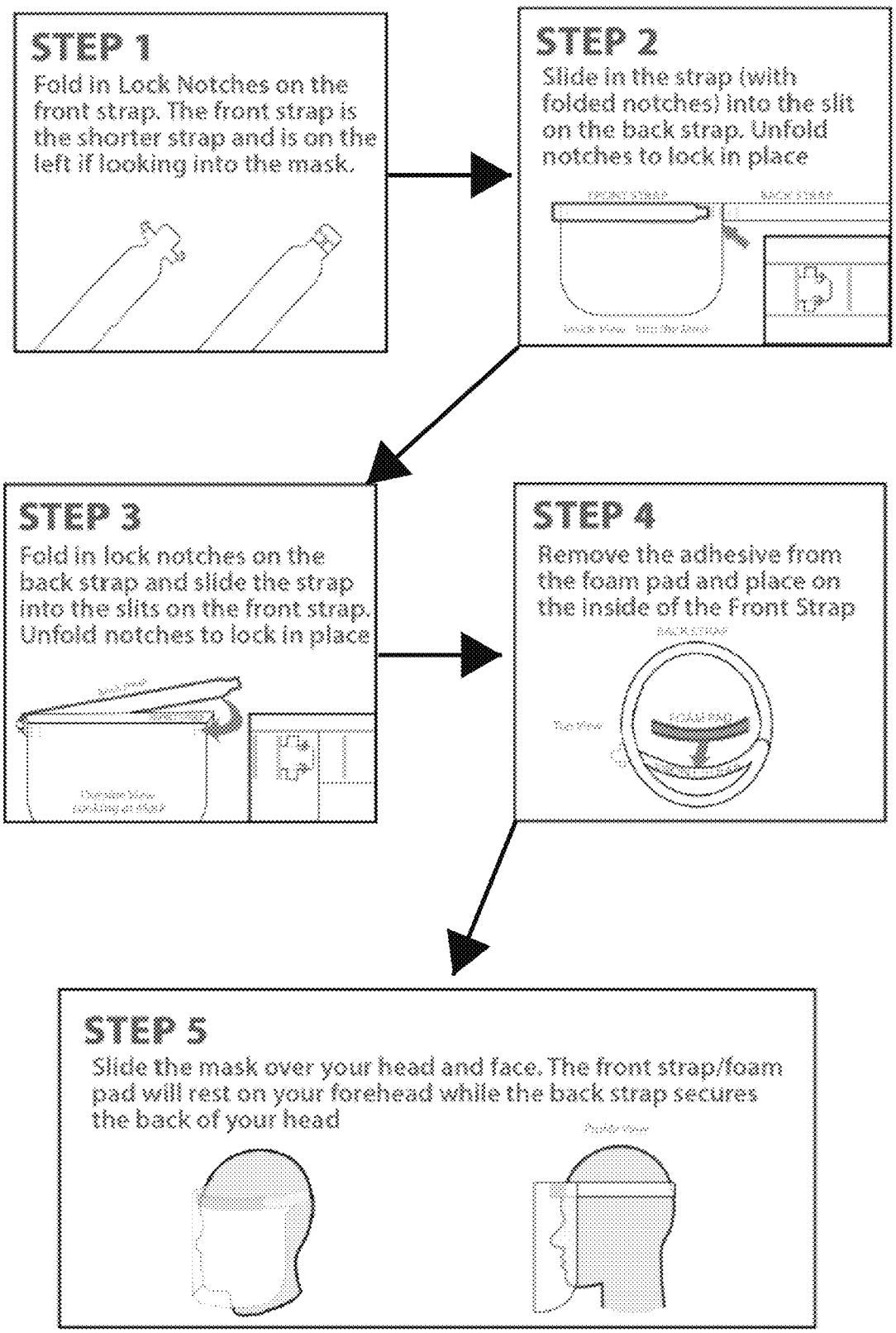
FIG. 12 shows a method of using the face shield shown in FIG. 6.

FIG. 12 shows a method of assembling the face shield 200 and attaching the face shield 200 to a head H. In Step 1, the front strap 204, which will go across the forehead, is bowed behind the transparent shield panel 202 and the front strap attachment feature 208 is inserted into one of the transparent shield panel attachment slots 212. In Step 2, the back strap 206 is bowed and the transparent shield panel attachment slot 214 is selected that fits the head size, and the back strap attachment feature 210 is slid into the transparent shield panel attachment slot 214. In Step 3, slide the finished face mask 200 over the head H and face. The front strap 204 will go across the forehead, flexing in a spring-like manner as it makes contact and conforms with the forehead, and the back strap 206 will go behind the head H to hold the face shield 200 on the head H.

Figure 13:
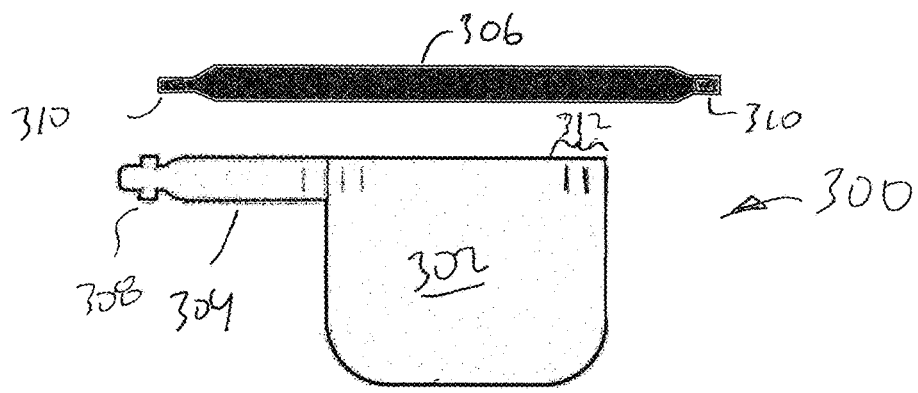
FIG. 13 is a front view showing another embodiment of a face shield.

FIG. 13 is a front view showing another embodiment of a face shield 300 that is a two piece design having a transparent shield panel 302 with an integral front strap 304, and a back strap 306. The transparent shield panel 302 is preferably made of a flexible plastic material and is sized to cover to width of the face and extend from the forehead to chin. The front strap 304 includes a first end 304a and a second end. The first end 304a integrally extends outwardly from the first side edge 302a of the transparent shield panel 302, and an opposite second end 304b having a front strap attachment lock notch or lock tab 308 configured to slide into a transparent shield panel attachment slot 312.

The front strap 304 is designed to be bowed toward the interior or face side of the transparent shield panel 302 with the front strap attachment lock notch or lock tab 308 coupling with the transparent shield panel attachment slot 312 proximate the second side edge 102b of the transparent shield panel 102, creating a space between them, forming a distance D between the transparent shield panel and the front strap 304. The distance D is selected to position the face shield away from a person's face so that it does not contact any face features, such as the nose or glasses.

The back strap 306 includes a first end 306a and a second end 306b. The first end 306a being coupled to the second side edge 302b of the transparent shield panel 30,2 and the second end 306b is coupled to the first side edge 302b of the transparent shield panel 302 using known attachment methods, such as bonding, welding, gluing, riveting, stapling, fastening, Velcro, etc.

Figures 18A, 18B:
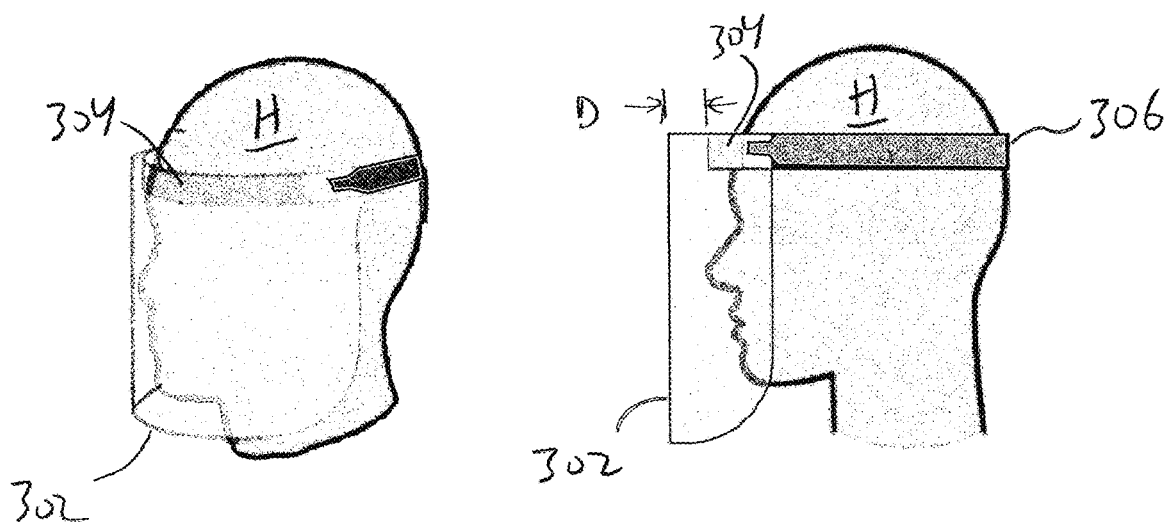
FIGS. 18A-18B are perspective and side views showing the face shield attached to a head H.

The front strap 304 is designed to contact the forehead and positions the transparent shield panel 302 away from the face a distance D (see FIG. 18B). The front strap 304 is made of materials that provide flexibility and some rigidity so that front strap 104 may conform to the contours of the forehead. The front strap 304 includes adjustment features to vary the distance D so that the transparent shield panel 302 does not contact any face features, such as the nose.

The shield panel 302 and front strap 304 may be made using a lightweight clear flexible sheet material that is optically clear such as PVC, PET, PETG, OPS, Polycarbonate and APET. It is also desirable that the flexible material is sufficiently rigid to be self-supporting when bowed in a cylindrical shape to cover the face without collapsing. The thickness of the material will depend on the particular material used to ensure sufficient flexibility without sacrificing the need of the material to be self supporting. The material selected is generally inexpensive such that the shield can be manufactured or fabricated at a low cost and be disposed of after each use. The rear strap 306 may be made of flexible, stretchable material, like elastic material.

Figures 14A, 14B:
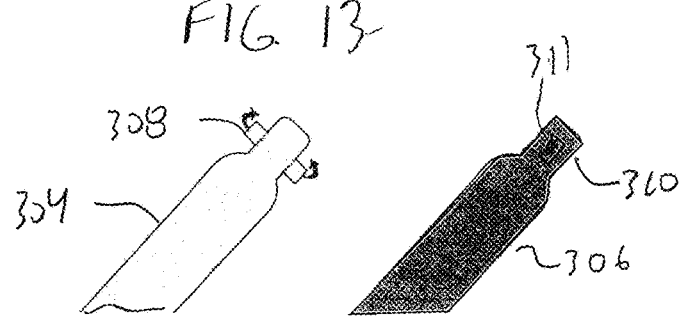
FIG. 14A shows the attachment feature of the front strap.
FIG. 14B shows the attachment features of the back strap.

FIG. 14A shows the attachment lock notches or lock tabs 308 of the front strap 304. In the open position, the attachment lock notches or lock tabs 308 are too wide the slide into transparent shield panel attachment slot 312. Prior to sliding into transparent shield panel attachment slot 312, front strap attachment lock notches or lock tabs 308 are prepared by bending or folding them inward toward each other, the same as shown in FIG. 7B. The allows front strap attachment lock notches or lock tabs 308 to slide easily into transparent shield panel attachment slot 312. Once through the transparent shield panel attachment slot 312, the front strap attachment lock notches or lock tabs 308 are unfolded or bent open to prevent front strap pullout, thereby locking the attachment lock notches or lock tabs 308 in the attachment slot 312, shown in FIG. 15B. If the size needs to be changed, the front strap attachment lock notches or lock tabs 308 may be bent or folded again and then withdrawn from the transparent shield panel attachment slot 312.

FIG. 14B shows the back strap attachment feature 310 includes a back strap coupling means 311 configured to attach to transparent shield panel coupling means 303 proximate the first side edge 302a, and second side edge 302b In some embodiments, the back strap 306 is fixedly coupled with the shield panel using known means, such as adhesive or Velcro. In some embodiment, one of the back strap coupling means 311 may be fixedly attached to shield panel coupling means 303 and the other back strap coupling means 311 may be removably attached to the opposite shield panel coupling means 303.

Figure 15A:
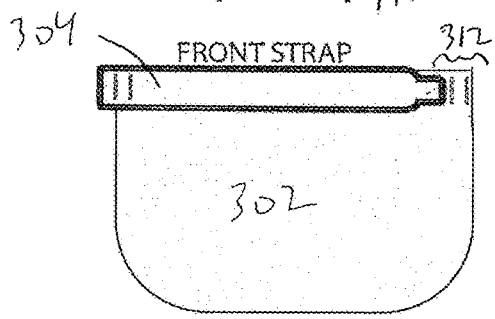
FIG. 15A is an inside view looking into the mask showing attachment of the front strap and FIG. 15B is an enlarged view showing engagement of the attachment feature with attachment slot.
Figure 15B:
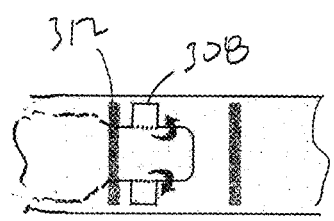

FIG. 15A is an inside view looking into the mask showing attachment of the front strap 304 and FIG. 15B is an enlarged view showing engagement of the attachment lock notches or lock tabs 308 with transparent shield panel attachment slot 312. The front strap 304 to designed to contact the forehead and position the transparent shield panel 302 a distance D away from the face. The front strap 304 is made of materials that provide flexibility and some rigidity so that front strap 304 may conform to the contours of the forehead. The front strap 304 includes an adjustment feature to vary the distance D so that the transparent shield panel 302 does not contact any face features, such as the nose.

To start assembly of face shield 300, front strap 304 is bowed on the face side of transparent shield panel 302 and front strap attachment lock notches or lock tabs 308 is inserted into one of the transparent shield panel attachment slots 312. Once the attachment lock notches or lock tabs 308 is inserted through the selected transparent shield panel attachment feature 312, the notches or lock tabs 308 are unfolded to lock it in the attachment slot 312, shown in FIG. 15B. There are multiple front strap attachment slots 312 to provide various offsets or distance D of the transparent shield panel from the face. If the size needs to be changed, the attachment lock notches or lock tabs 308 may be bent or folded again and then withdrawn from the attachment slot 312.

Figures 16A, 16B:
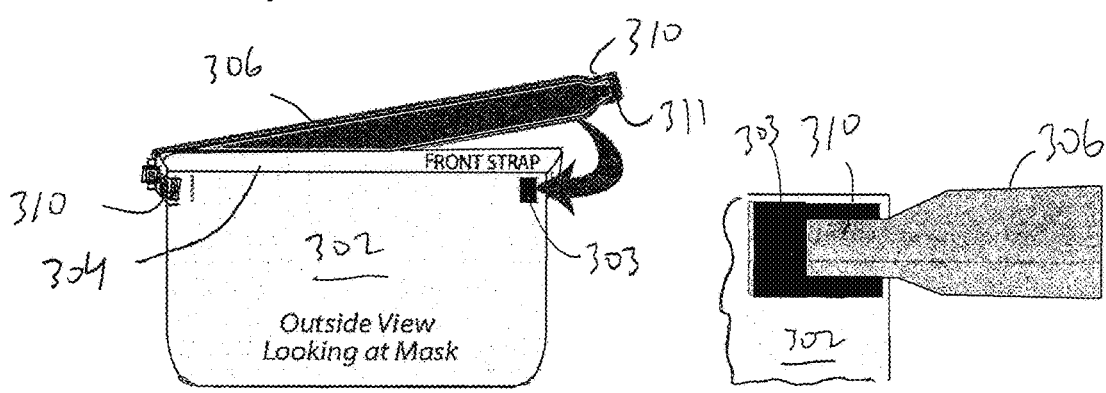
FIG. 16A is an outside view looking at face mask showing attachment of the back strap.
FIG. 16B is an enlarged view showing engagement of the attachment feature with shield panel using attachment means.

FIG. 16A is an outside view looking at face mask 300 showing attachment of the back strap 306, and FIG. 16B is an enlarged view showing engagement of the attachment feature 310 with shield panel 302 using transparent shield panel attachment means 303. The back strap 306 to designed to go around the back of the head H to hold the face shield 300 on the head (see FIGS. 18A, 18B). The back strap 306 is made of stretchable/flexible materials that form to the contours around head. The back strap 306 includes back strap attachment means 311 configured to couple with the shield panel attachment means 303 and the stretchable/flexible materials vary sizing of the face shield 300 to fit different size heads.

The back strap 306 is attached to the transparent shield panel 302 after the front strap 304. One end of the back strap 306 is coupled to the transparent shield panel attachment means 303 proximate first side edge 302a and the end of the back strap 306 is coupled to the transparent shield panel attachment means 303 proximate second side edge 302b, shown in FIGS. 16B, 16C.

Figure 17:
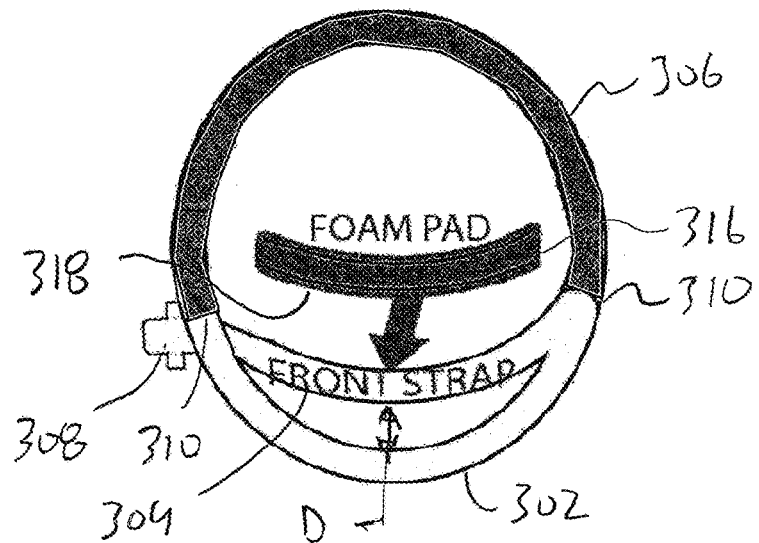
FIG. 17 is a top view showing the assembled face shield.

FIG. 17 is a top view showing the assembled face shield 300. The front strap 304 is bowed on the rear or face side of transparent shield panel 302. The distance D may be varied by sliding the front strap attachment lock notches or lock tabs 308 into the various front strap attachment slots 312. When the desired distance is achieved, the front strap attachment lock notches or lock tabs 308 is unfolded in the desired front strap attachment slot 312, locking the front strap 304 in place. The back strap attachment means 311 is coupled to shield panel 302 using attachment means 303. Using a removable back strap attachment means 311 and transparent shield panel attachment means 303 allows the back strap 306 to be changed for a different size. In some embodiments, the back strap 306 may be personalized with a name or design, or be a different color.

An optional pad 316 may be used inside the front strap 304 to contact the head H. The pad 316 includes an attachment material 318 that is used to attach the pad 316 with the front strap 304. The pad 316 may be made of different material depending on the application. The strap may be made of a soft material for comfort, made of a frictional material to prevent slippage of the face mask 300 on the head, or made of an absorbent material to soak up sweat to keep it out of the eyes, similar to a headband. In the embodiment shown, the pad 316 is a foam material. The attachment material 318 may be an adhesive material, such as an adhesive strip, or may be a Velcro material so the pad 316 removable or replaceable.

FIGS. 18A-18B are perspective and side views showing the face shield 300 attached to a head H. In use, the front strap 304 is bowed and the front strap attachment lock notches or lock tabs 308 is inserted into the desired front strap attachment slot 312. The back strap attachment means 311 is coupled to transparent shield panel 302 using transparent shield panel attachment means 303. The transparent shield panel 302 is then positioned on the face and pushed inward slightly with the front strap 304 flexing in a spring-like manner as it makes contact and conforms with the forehead. The back strap 306 is pulled over the top of the head to contact and conform the rear and sides of the head to hold the face shield 300 on the head H.

While embodiments and applications of this invention have been shown and described, it would be apparent to those skilled in the art that many more modifications than mentioned above are possible without departing from the inventive concepts herein. It is to be understood that the present disclosure is illustrative only and that changes, variations, substitutions, modifications and equivalents will be readily apparent to one skilled in the art and that such may be made without departing from the spirit of the invention as defined by the following claims.

The invention claimed is:

1. A one-piece protective face shield comprising:
a transparent shield panel, an integral front and an integral back strap made using a clear flexible sheet material that is optically clear:
the transparent shield having a first side edge, a second side edge, and multiple transparent shield panel attachment slots proximate the first side edge and the second side edge;
the front strap having a first end and a second end, the first end integrally extending outward from the first side edge, and the second end having a front strap attachment lock tab configured to slide into one of the multiple transparent shield panel attachment slots proximate the second side edge and lock in place; and
the back strap having a first end and a second end, the first end integrally extending outward from the second side edge, and the second end having a back strap attachment lock tab configured to slide into one of the multiple transparent shield panel attachment slots proximate the first side edge and lock in place to hold the protective face shield on a person's head.

2. The protective face shield of claim 1, wherein coupling the front strap attachment lock tab to the transparent shield panel attachment slot or slit creates a space between the front strap and the transparent shield panel, wherein the space is configured to position the transparent shield panel a distance D away from a person's face.

3. The protective face shield of claim 2, wherein lengthening or shortening the front strap varies the distance D away from the person's face.

4. The protective face shield of claim 2, wherein coupling the front strap attachment lock tab to different ones of the multiple transparent shield panel attachment slots varies the distance D away from the person's face.

5. The protective face shield of claim 1, wherein prior to sliding into the multiple transparent shield panel attachment slots, the front strap attachment lock tab and the back strap attachment lock tab are prepared by bending or folding inward to allow them to slide into the attachment slots, then once through, bent open or unfolded to prevent pullout, thereby locking the front strap attachment lock tab and the back strap attachment lock tab in the corresponding transparent shield panel attachment slot.

6. The protective face shield of claim 1, wherein the transparent shield panel, the front strap, and the back strap are made of an optically clear flexible sheet material.

7. The protective face shield of claim 1, wherein the transparent shield panel is made of an optically clear material and the front strap and/or the back strap are made from a non-optically clear material.

8. The protective face shield of claim 1, further comprising a pad coupled to the front strap to configured to contact the person's forehead.

9. The protective face shield of claim 8, wherein the pad may be made of a frictional material configured to prevent slippage of the face mask on the person's forehead.

10. The one-piece protective face shield of claim 1, further comprising a pad coupled to the front strap configured to contact the person's forehead.

11. The one-piece protective face shield of claim 10, wherein the pad may be made of a frictional material configured to prevent slippage of the face mask on the person's forehead.

12. A protective face shield comprising:
a transparent shield panel, an integral front strap and an integral back strap made using a flexible sheet material that is optically clear:
the transparent shield panel includes a first side edge, a second side edge, and multiple transparent shield panel hook and loop attachment features proximate the first side edge and the second side edge;
the front strap having a first end and a second end, the first end integrally extending outward from the first side edge, and the second end having a front strap hook and loop attachment feature configured to couple with one of the multiple transparent shield panel hook and loop attachment features proximate the second side edge; and
the back strap having a first end integrally extending outward from the second side edge and a second end having a hook and loop attachment feature configured to couple with one of the transparent shield panel hook and loop attachment features proximate the first side edge to hold the protective face shield to a person's head,
wherein coupling the front strap hook and loop attachment feature to the transparent shield panel hook and loop attachment feature creates a space between the front strap and the transparent shield panel, wherein the space configured to position the transparent shield panel a distance D away from a person's face.

13. The protective face shield of claim 12, wherein lengthening or shortening the front strap varies the distance D away from the person's face.

14. The protective face shield of claim 12, wherein coupling the front strap hook and loop attachment feature to different ones of the multiple transparent shield panel hook and loop attachment feature varies the distance D away from the person's face.

15. The protective face shield of claim 12, wherein the transparent shield panel, the front strap and the rear strap are made of an optically clear flexible sheet material.

16. The protective face shield of claim 12, wherein the transparent shield panel is made of an optically clear material and the front strap and/or the back strap are made from a non-optically clear material.

17. The one-piece protective face shield of claim 12, further comprising a pad coupled to the front strap configured to contact the person's forehead.

18. The one-piece protective face shield of claim 17, wherein the pad may be made of a frictional material configured to prevent slippage of the face mask on the person's forehead.

19. A one-piece protective face shield comprising:

a transparent shield panel, an integral front and an integral back strap made using a clear flexible sheet material that is optically clear;

the front strap having a first end integrally extending outward from a first side edge of the transparent shield panel and a second end configured to adhesively couple with a second side edge of the transparent shield panel; and the back strap having a first end integrally extending outward from the second side edge of the transparent shield panel and a second end configured to adhesively couple with the first side edge of the transparent shield panel to hold the protective face shield to a person's head;

wherein adhesively coupling the front strap to the transparent shield panel creates a space between the front strap and the transparent shield panel, wherein the space configured to position the transparent shield panel a distance D away from a person's face.

20. The one-piece protective face shield of claim 19, wherein the distance D may vary by changing a length of the front strap.

* * * * *